United States Patent [19]
O'Sullivan

[11] Patent Number: 5,367,731
[45] Date of Patent: Nov. 29, 1994

[54] THERAPEUTIC PILLOW HAVING AN EXTERIOR DEPRESSION ON ONE SIDE FOR PROVIDING DIFFERENT DEGREES OF SUPPORT TO A USER'S NECK

[76] Inventor: Dennis C. O'Sullivan, 123 Juanita, Unit 1-4, Incline Village, Nev. 89451

[21] Appl. No.: 986,360

[22] Filed: Dec. 7, 1992

Related U.S. Application Data

[63] Continuation-in-part of Ser. No. 590,659, Sep. 28, 1990, Pat. No. 5,168,590.

[51] Int. Cl.⁵ ............................................. A47C 20/02
[52] U.S. Cl. ............................................ 5/645; 5/636
[58] Field of Search ..................... 5/636, 637, 639, 640, 5/645, 485

[56] References Cited

U.S. PATENT DOCUMENTS

| | | | |
|---|---|---|---|
| D. 282,427 | 2/1986 | O'Sullivan | D6/601 |
| D. 295,936 | 5/1988 | Sanders | D6/601 |
| D. 298,198 | 10/1988 | O'Sullivan | D6/601 |
| 3,143,748 | 8/1964 | Manning | 5/344 |
| 3,243,828 | 4/1966 | McCarty | 5/338 |
| 3,261,035 | 7/1966 | Slocum | 5/636 |
| 3,279,849 | 10/1966 | Radke et al. | 297/284 |
| 3,542,421 | 11/1970 | Ambrose | 297/230 |
| 3,638,251 | 2/1972 | Weiss | 5/334 |
| 3,849,810 | 11/1974 | Degen | 5/341 |
| 4,231,125 | 11/1980 | Tittl | 5/419 |
| 4,309,784 | 1/1982 | Cohen | 5/442 |
| 4,413,368 | 11/1983 | Schuetze | 5/494 |
| 4,513,462 | 4/1985 | Thomas | 5/645 |
| 4,655,502 | 4/1987 | Houllis | 297/229 |
| 4,666,207 | 5/1987 | Quartano | 297/229 |
| 4,679,848 | 7/1987 | Spierings | 297/284 |
| 4,682,691 | 7/1987 | Spiering | 206/373 |
| 4,688,286 | 8/1987 | Miker, Jr. | 5/490 |
| 4,754,513 | 7/1988 | Rinz | 5/485 |
| 4,783,866 | 11/1988 | Simmons et al. | 5/441 |
| 4,853,994 | 8/1989 | Ekstein | 5/437 |
| 4,862,536 | 9/0589 | Pruit | 5/432 |
| 4,864,668 | 9/1989 | Crisp | 5/432 |
| 4,876,755 | 10/1989 | Parrish | 5/431 |
| 4,908,894 | 3/1990 | Sanders | 5/645 |
| 4,941,222 | 7/1990 | Prager | 5/111 |
| 4,945,589 | 8/1990 | Carey | 5/442 |
| 4,949,411 | 8/1990 | Tesch | 5/434 |
| 5,088,141 | 2/1992 | Meyer | 5/636 |
| 5,168,590 | 12/1992 | O'Sullivan | 5/490 |

FOREIGN PATENT DOCUMENTS

| | | | |
|---|---|---|---|
| 302426 | 2/1989 | European Pat. Off. | 5/645 |
| 1127948 | 12/1956 | France | 5/337 |
| 3138463A1 | 4/1983 | Germany . | |
| 16809 | of 1908 | United Kingdom . | |
| 26072 | of 1909 | United Kingdom . | |
| 1837 | of 1912 | United Kingdom | 5/490 |
| 1590583 | 6/1981 | United Kingdom . | |

Primary Examiner—Flemming Saether
Attorney, Agent, or Firm—Limbach & Limbach

[57] ABSTRACT

A two-sided pillow that is capable of providing different degrees of support to a user's neck is disclosed. In one embodiment, pillow fill is enclosed between a first and a third panel. An exterior depression is formed in the central region of the first panel, and the central region of the third panel is supported in a substantially flat position. In another embodiment, pillow fill is enclosed between first and second opposed panels. Each of the first and second panels has a depression formed substantially at a central region thereof. A third panel is attached to the second panel for covering the depression formed in the second panel, and pillow fill is enclosed between the third panel and the second panel. In another embodiment, first and second opposed panels that are substantially identical and that each have a central region and four sides are joined together along the four sides to enclose pillow fill therebetween. The first and second panels are further joined together at the central region of each panel to form an exterior depression substantially at the center of each panel. A third panel is attached to the second panel for covering the exterior depression formed in the second panel, and pillow fill is enclosed between the third panel and the second panel.

6 Claims, 7 Drawing Sheets

THERAPEUTIC PILLOW HAVING AN EXTERIOR DEPRESSION ON ONE SIDE FOR PROVIDING DIFFERENT DEGREES OF SUPPORT TO A USER'S NECK

CROSS-REFERENCE TO RELATED APPLICATION

This application is a continuation-in-part of applicant's co-pending application Ser. No. 07/590,659, filed Sep. 28, 1990, which application has issued as U.S. Pat. No. 5,168,590.

TECHNICAL FIELD

The present invention relates broadly to pillow coverings and pillows, and, more particularly, to a two-sided pillow for providing support to a user's neck which may include one or more pockets for holding pillow inserts or hot/cold packs.

BACKGROUND ART

Orthopedic pillows and pillow cases have been developed to support the head and neck. U.S. Pat. No. 4,754,513 to Rinz, for example, discloses a pillow case with a single compartment, extending the length of one of the long sides of a standard rectangular pillow, for holding an elastomeric insert. The insert is designed to support a person's neck. However, the pillow case does not provide support for the side of the person's head and does not provide a way for the user to adjust the thickness of the center region of the pillow, the sides of the pillow, the top of the pillow, or the bottom of the pillow.

Orthopedic pillows having several sections have also been developed. However, these pillows and pillow covers tend to be bulky and cumbersome. For example, U.S. Pat. No. 3,849,810 to Degen shows a pillow and pillow case made up of three interconnecting sections of equal size. Each section is separated by a vertical cut which extends part-way down the pillow and pillow case. The central section is about half as thick as the other two sections. By adding an additional panel capable of being rolled up, to the central section of the pillow case, the pillow maybe modified to include a neck roll. The disadvantage with the Degen pillow is that forming the neck roll section is cumbersome. The user has to roll up the panel and place it in a compartment in the pillow case. Another disadvantage of the Degen pillow is that the rolled up panel may come unrolled while it is being used.

Some of orthopedic pillows have two parallel neck roll compartments. German Patent DE 3138463 A1 to Jackle for instance shows a pillow case having two compartments for holding a support pillow which extends for the entire length of the pillow case. While the dual parallel compartments provide a place to hold head and neck support pillows a user does not have the ability to adjust the thickness of other parts of the pillow (e.g., the depth of the center of the pillow where the user places his head or the thickness of the short sides of the pillow).

SUMMARY OF THE INVENTION

The present invention is directed to a two-sided pillow that is capable of providing different degrees of support to a user's neck. In one embodiment, the two-sided pillow includes a first panel, a third panel, and pillow fill enclosed between the first and third panels. An exterior depression is formed in the central region of the first panel, and the central region of the third panel is supported in a substantially flat position.

In another embodiment, the two-sided pillow includes a pillow having first and second opposed panels with pillow fill enclosed therebetween. Each of the first and second panels has a depression formed substantially at a central region thereof. A third panel is attached to the second panel for covering the depression formed in the second panel, and pillow fill is enclosed between the third panel and the second panel.

In another embodiment, the two-sided pillow includes a pillow having first and second opposed panels that are substantially identical and that each have a central region and four sides. The first and second panels are joined together along the four sides and enclose pillow fill therebetween. The first and second panels are further joined together at the central region of each panel to form an exterior depression substantially at the center of each panel. A third panel is attached to the second panel for covering the exterior depression formed in the second panel, and pillow fill is enclosed between the third panel and the second panel.

A better understanding of the features and advantages of the present invention will be obtained by reference to the following detailed description of the invention and accompanying drawings which set forth an illustrative embodiment in which the principles of the invention are utilized.

DETAILED DESCRIPTION OF THE PREFERRED

Figure 1:
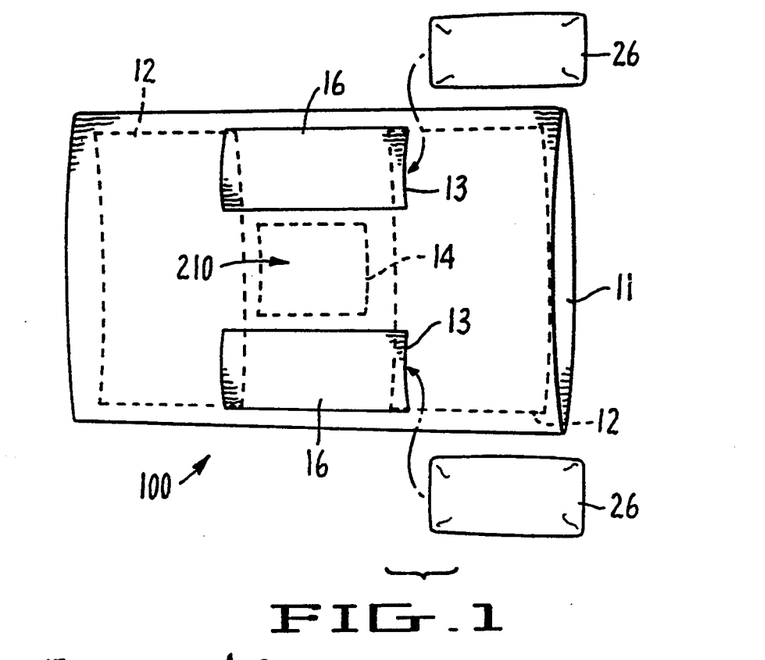
FIG. 1 is a front perspective view of the pillow cover of present invention.
Figure 2:
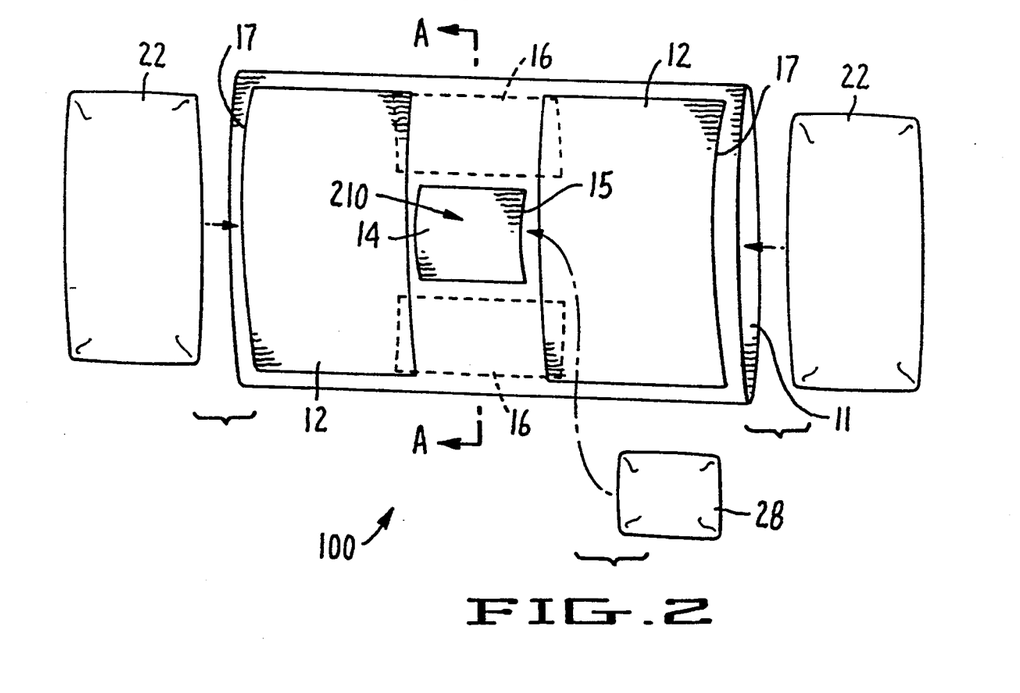
FIG. 2 is a back perspective view of the pillow cover shown in FIG. 1.
Figures 3, 4, 5:
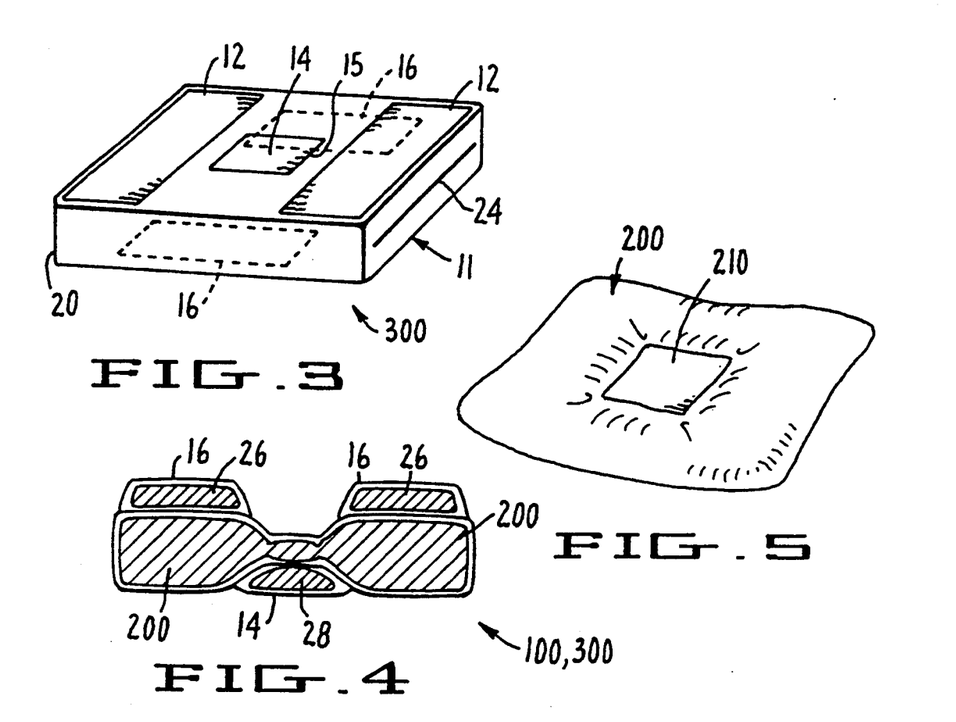
FIG. 3 is an alternative back perspective view of the pillow cover of the present invention having boxed corners.
FIG. 4 is a sectional view taken along line A—A of FIG. 2.
FIG. 5 is a top, front perspective view of a conventional therapeutic pillow having a central depression region.

Referring to FIGS. 1, 2 and 5 a therapeutic pillow cover 100, also referred to as a cover element, for covering either a prefabricated pillow or for serving as a shell for encasing pillow fill to form a pillow, is illustrated. While the pillow cover 100 may be used to cover a conventional pillow, it is preferably used to cover a health pillow 200 as shown in FIG. 5 and in U.S. Pat. No. Des. 282,427 and having a central, padded depression region or center pocket 210. The pillow cover 100 has an open end 11 to permit the pillow 200 to be inserted and removed from the cover 100. As illustrated, the pillow cover 100 is rectangular, however, it may be any shape: round, square, oval, triangular or trapezoidal.

In the preferred embodiment, the pillow cover 100 has five compartments: a center compartment 14, two oppositely disposed hot/cold pack compartments 16, and two oppositely disposed side wing compartments 12. Compartments 12, 14, 16 permit a person to change the elevation and curvature of separate regions of a pillow to derive maximum support and comfort.

The center compartment 14 is attached on a first back side of the pillow cover 100 in about the center of the cover 100. The center compartment is stitched to the cover 100. When a person lies on the pillow cover 100, his head rests approximately in the central depression region 210 and on the center compartment 14. The center insert 28 permits the user to have the option to adjust the thickness of the central depression region 210 (or in general, the depth of the central region of a pillow) to achieve a more desirable comfortable level.

The center compartment 14 is about the same size and shape as, or larger than the central depression region 210 of the pillow 200 that is to be covered.

In the preferred embodiment, the center compartment 14 is rectilinear-shaped. However, the size and shape of the center compartment 14 may be varied to accommodate central depression regions 210 of different sizes and shapes. (e.g., rectangular regions, trapezoidal regions, squares, ovals, circles, etc). As illustrated, two sides of the insert 28 are parallel to the two long sides of the pillow cover 100.

The pillow cover 100 also has a pair of front side hot/cold pack compartments 16, one being located in the top region and the other being located in the bottom region. Each of the hot/cold pack compartments 16 is centered along the long side of the pillow cover 100 opposite from one another. The hot/cold pack compartments 16 are rectangular shaped. Their long sides are attached to the pillow cover 100 parallel to the long side of the cover. The hot/cold pack compartments 16 are preferably about one half as long as the long side of the pillow cover 100. Short side of the compartment 16 generally extends from about the exterior edge of the pillow cover 100 to about the edge of the center compartment 14.

The compartments 16 have an opening 13 from which a hot/cold pack 26 or a pillow insert may be inserted or removed. At least two of the edges of the compartment 16 are stitched to the cover 100. In the preferred embodiment, one of the short ends 13 of the compartment 16 is left open to permit the insertion and removal of the hot/cold pack 26. The open end 13 may be fastened closed via conventional fasteners such as Velcro, snaps, zipper, buttons, etc.

In the illustrated embodiment the hot/cold pack compartments 16 are attached on a second front side of the pillow cover 100 as shown in FIG. 1 and the perimeter of the hot/cold pack compartments 16 are shown in phantom in FIG. 2. In alternate embodiments, the center compartment 14 and hot/cold pack compartments 16 may be attached on the same side of the pillow cover 100.

The pillow covering 100 also has a pair of side wing compartments 12; one side wing compartment 12 is attached in the left region while the other side wing compartment 12 is attached in the right region. The compartments 12 are rectangular shaped and are attached to the cover 100 with their long sides parallel to the short sides of the pillow cover 100. The side wing compartments 12 may be attached on the same side of the pillow cover 100 or on opposite sides. As illustrated, the pair of side wing compartments 12 are attached on the same back side of the pillow cover 100 across form one another and also attached on the same side as the center compartment 14. Hence, the center compartment is 14 in between the side wing compartments 12.

The length of the short sides of the compartment 12 is about equal to one third of the length of the pillow cover 100.

The side wing compartments 12 are stitched to pillow cover 100 on three sides and open on one side 17 to permit therefrom a pillow insert to be inserted and removed. The pillow insert 22 helps support a person's face when he is laying on his side. The open ends of the compartments may be fastened together using a strip of Velcro.

Figure 8:
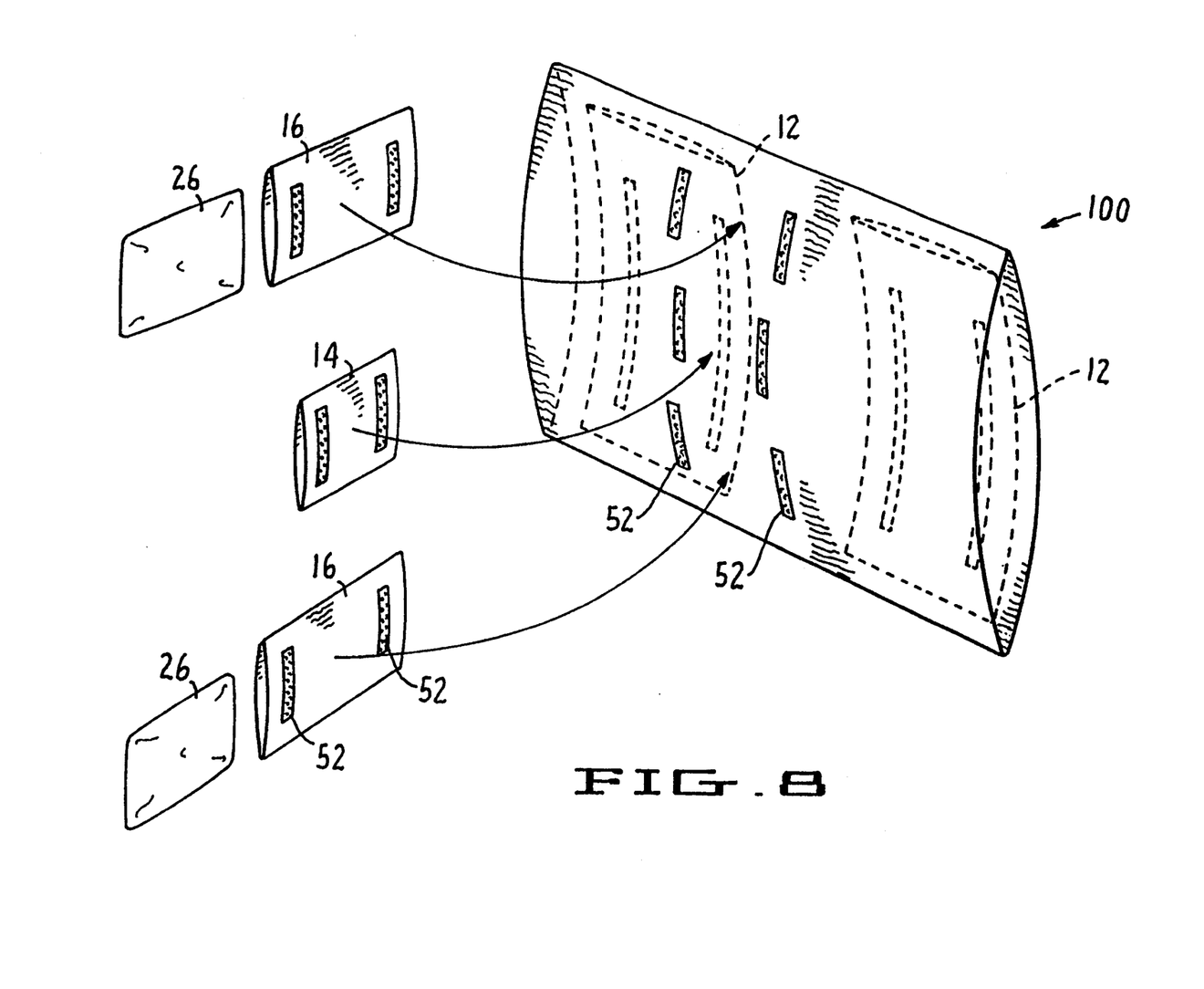
FIG. 8 is a perspective view of the pillow cover illustrating the compartments fastened on the interior of the pillow cover and a removable compartment.

In the preferred embodiment, where the pillow cover 100 is used as a pillow case to cover a prefabricated pillow, the compartments 12, 14, 16 are permanently affixed to the cover 100 on the interior of the pillow cover 100. FIG. 8 illustrates the side wing compartments 12 fastened to interior wall 50 of pillow cover 100. However, the compartments 12, 14, 16 may be sewn on the cover's exterior.

Referring to FIG. 3, pillow cover 300 having boxed corners 20 is illustrated. The pillow cover 300 may be used as a pillow case to cover either a conventional pillow, or more preferably, the health pillow 200. The boxed off corners 20 give the pillow cover more depth so that the pillow that is covered is not compressed when it is housed inside the cover 300. Hence the boxed off corners 20 protect the pillow from having its shape substantially altered.

The pillow cover 300 also has an open end 11 where the pillow to be encased is inserted/removed. The opening may also be closed by Velcro or other fasteners such as a zipper, snaps, buttons, etc.

Alternate embodiments of the pillow cover 100 may have the compartments 12, 14, 16 removably attached to the pillow cover 100 via snaps, fasteners, Velcro or the like, either on the interior or the exterior of the pillow cover 100. FIG. 8 illustrates one method of removably attaching the compartments 16 to the pillow cover 100 by way of Velcro strips 52. Velcro strips 52 are mounted on one side of the compartment 16, as well as the pillow cover 199 where compartment 16 is to be attached. Compartment 16 is easily attached to the pillow cover 100 by pressing it against same.

When the pillow cover 100 is used as the shell, to contain pillow fill making up a sleeping pillow, it is preferable for the compartments 12, 14, 16 to be located on the exterior of the pillow cover 100.

Referring to FIG. 4, a cross sectional view of the pillow cover 100, 300 showing the pillow 200 and the inserts 28, 26 is illustrated. The center pillow insert 28 is housed in the center compartment 14 and is in alignment with the central depression region 210 of the health pillow 200. The hot/cold pack compartments 16 contain the hot packs 26.

Figures 6, 7:
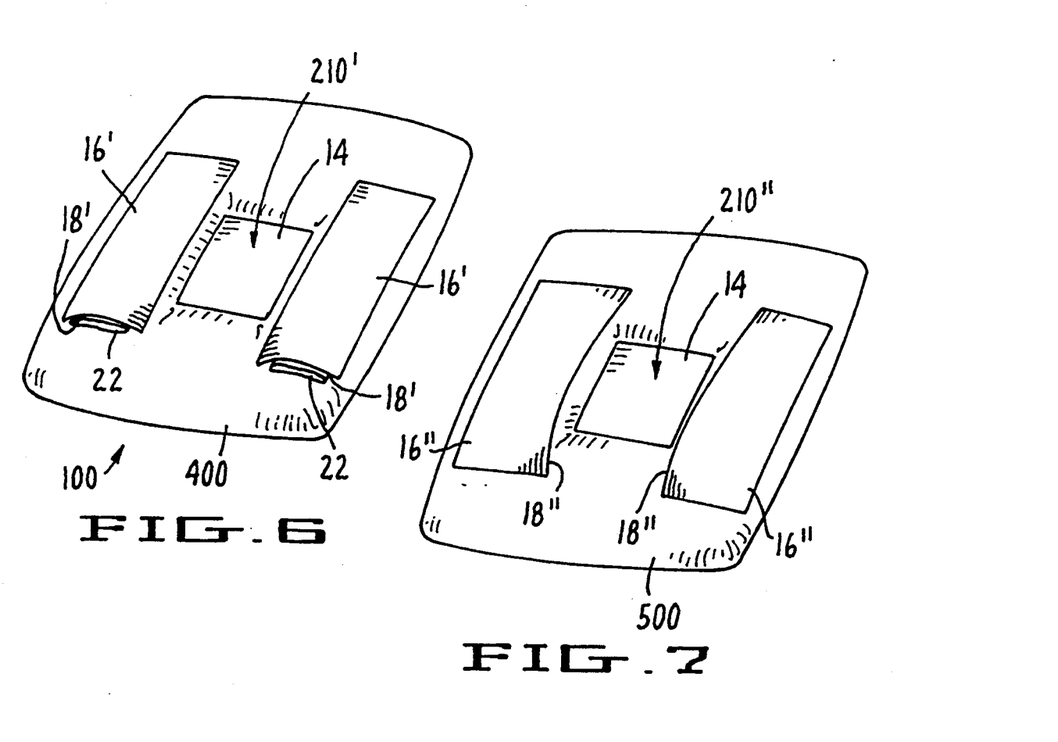
FIG. 6 is a back perspective view, similar to FIG. 2, of an alternate pillow cover encasing pillow fill.
FIG. 7 is a back perspective view, similar to FIG. 6 of yet another alternate pillow cover encasing pillow fill.

FIGS. 6 and 7 shows two alternate pillow covers 400, 500 respectively used as the shell for encasing pillow fill, thereby forming a health pillow 400, 500. As previously discussed, when the cover 100 is used to encase pillow fill, the compartments 12, 14, 16, are preferably attached to the exterior of the cover 100. The pillows 400, 500 have a center pocket or central depression region 210' and 210" respectively.

The center compartment 14 may be attached to the pillow cover over the central depression region 210. In the preferred embodiment, the compartment 14 is stitched to the central depression region. If the center compartment 14 is attached to the pillow cover, it may have an open side 15 to permit the central pillow insert 28 to be inserted/removed. Alternatively, the center pocket 14 may be formed by stitching the front and back panels together.

Referring to FIG. 6, the hot/cold pack compartments 16' are stitched to the cover 400 on at least two sides and has one of its short sides 18' open. Referring to FIG. 7, which is similar to FIG. 6, the hot/cold pack compartments 16" are stitched to the cover 500 on three sides and has one of its long sides 18" open.

The compartments 12, 14, 16 may include a pleat so that the compartment may be enlarged. In the preferred embodiments, the pillow cover 100, 400, 500 and the compartment attachments 14, 16, 18 are made out of the same material. However, the cover 100, 400, 500 and the compartments 12, 14, 16 may be fabricated out of different materials. For example, the compartments may be made out of an elastic material.

The health pillow 200 or a conventional pillow may be enhanced by the pillow user having the option of attaching any one, or a combination of, the compartments 14, 16, 18 directly onto the pillow 200 using any type of removable fastener, such as Velcro strips 52 illustrated in FIG. 8. To make the enhanced pillow more comfortable to sleep on, the enhanced pillow can be covered with a standard pillow case.

Figure 9:
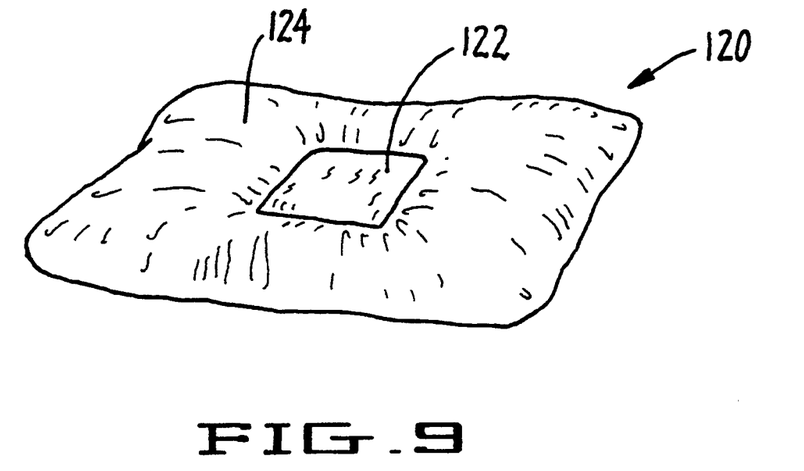
FIGS. 9 and 10 are perspective views illustrating the first and second sides of one embodiment of a two-sided pillow in accordance with the present invention.
Figure 10:
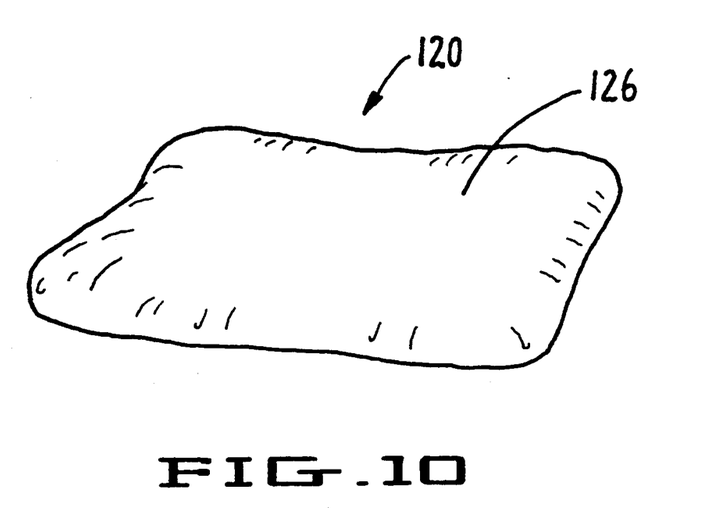
Figure 11:
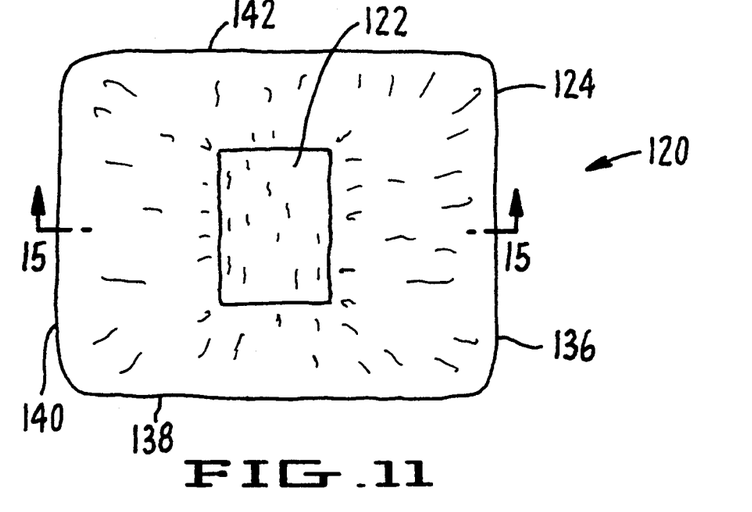
FIGS. 11 through 14 are top, bottom, and side views of the two-sided pillow of FIGS. 9 and 10.
Figure 12:
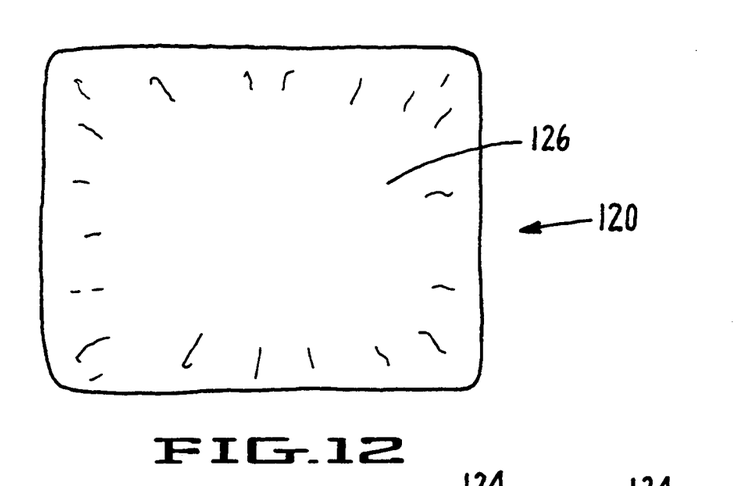
Figure 13:
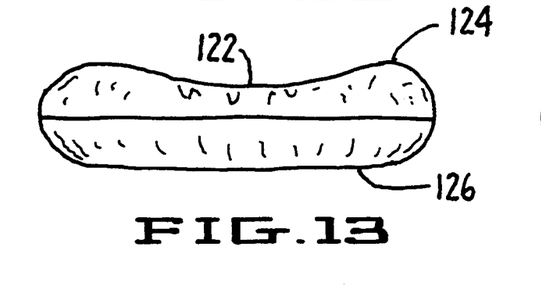
Figure 14:
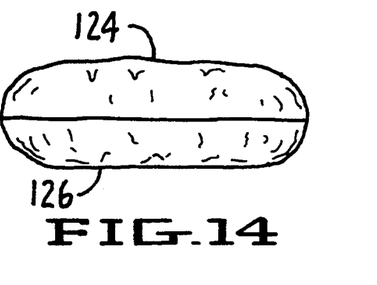

Referring to FIGS. 9 and 10, there is illustrated an embodiment of a two-sided pillow 120 in accordance with the present invention. The two-sided pillow 120 is particularly suited for providing two different degrees of support to a user's neck. The two-sided pillow 120 has a central depression 122 on its first side 124, as shown in FIG. 9, and is relatively flat on the second side 126, as shown in FIG. 10. The two-sided pillow 120 provides a first degree of support for a user's neck when the first side 124 is used, and a second degree of support when the second side 126 is used.

Specifically, when a user rests his or her head on the first side 124, the user's head sinks down into the central depression 122. The part of the pillow's first side 124 just outside the depression 122 makes firm contact with the user's neck and provides support thereto. When the pillow 120 is used in this manner, maximum support is provided to the neck.

If a user desires a smaller amount of support to his or her neck, the pillow's second side 126 may be used. When the user rests his or her head in the central region of the second side 126, the user's head sinks into the pillow less than when the first side 124 is used, but more than when a conventional pillow is used. The user's head sinks more than in a conventional pillow because the central depression 122 is directly below the user's head on the opposite side of the pillow 120. The presence of the central depression 122 reduces the amount of support given to the user's head by the pillow 120.

Because the user's head sinks into the pillow's second side 126 a small amount, the side portions of the pillow 120 come into contact with the user's neck to give support thereto. However, this contact is not as firm as when the pillow's first side 124 is used.

Many users find the reduced support of the pillow's second side 126 more comfortable during certain times, but at other times, the same users may prefer the firmer support given by the pillow's first side 124. Thus, the pillow 120 allows the user to adjust the amount of support given to his or her neck by simply turning the pillow 120 over to its other side.

Referring to FIGS. 11 through 15, an embodiment of the pillow 120 in accordance with the present invention may be constructed by using an additional panel 128 and pillow fill 130 to cover and fill one of the central depressions of any one of the Health Pillows disclosed in U.S. Pat. Nos. Des. 282,427 and Des. 298,198. The central region of the additional panel 128 is supported in a substantially flat position by means of the pillow fill 130. The additional panel 128 and the pillow fill 130 may cover the entire side of the Health Pillow or just the central depression.

Although the Health Pillow mentioned above is a preferred pillow for use in the two sided pillow 120, any pillow that includes a first panel 132 opposed to a second panel 134 may be used. Such a pillow's first and second panels 132 and 134 are preferably identical and preferably each have four sides 136, 138, 140 and 142. The first and second panels may be joined together along the four sides 136, 138, 140 and 142 to enclose pillow fill 144 therebetween. The corners where the four sides 136, 138, 140 and 142 intersect preferably define a rectangle. The four sides 136, 138, 140 and 142 may be substantially straight, convex shaped, or concave shaped. The Health Pillows disclosed in the above-referenced '427 and '198 design patents have concave shaped sides. Although the pillow 120 is preferably rectangular in shape, it should be well understood that it may be nearly any shape, such as circular, triangular, square, octagonal, etc.

Figure 15:
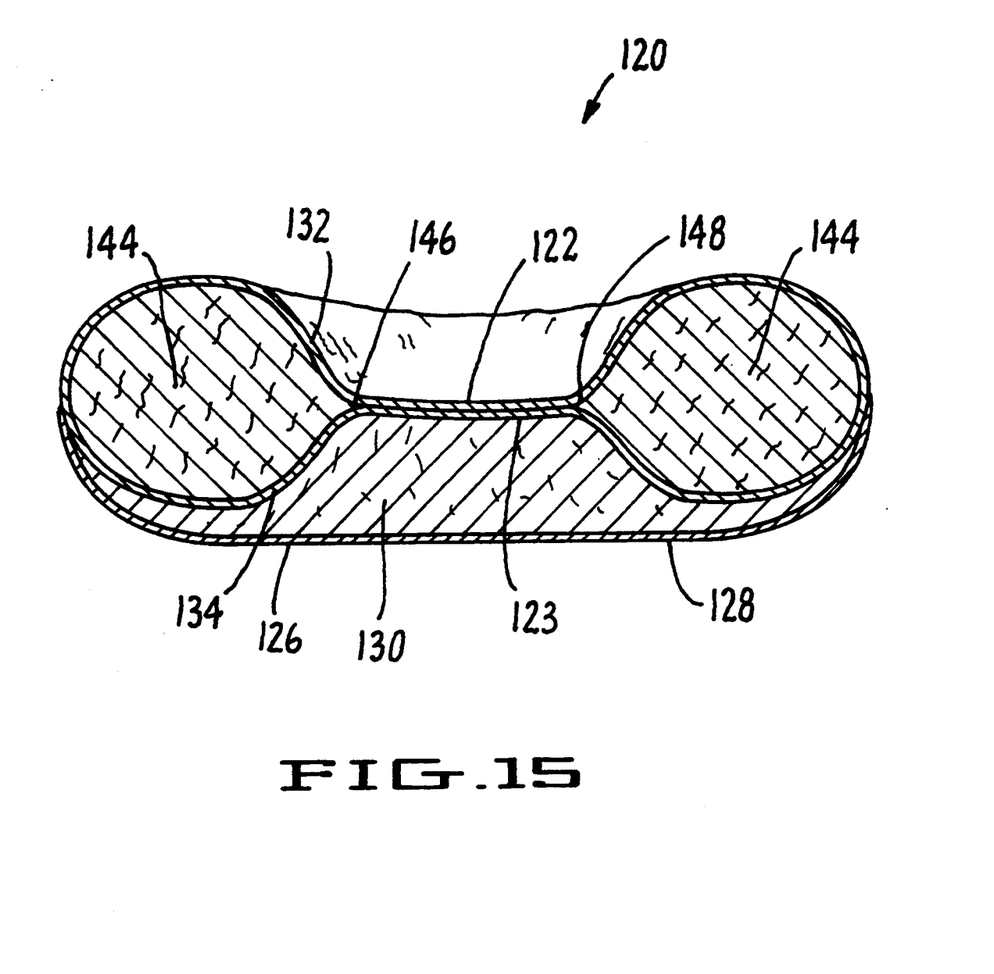
FIG. 15 is a cross-sectional view of the two-sided pillow of FIGS. 9 and 10.

The exterior central depression 122, as well as an exterior central depression 123 on the opposite side, are preferably formed by means of joining the central regions of the first and second panels 132 and 134 together at points 146 and 148. The points 146 and 148 are preferably joined or attached together by means of sewing, or the like, and preferably form part of rectangular or circular shaped exterior depressions 122 and 123. However, it should be well understood that the exterior depressions 122 and 123 may be of many different shapes, such as rectangular, circular, triangular, octagonal, etc. Some of these alternative shapes are disclosed in U.S. Pat. No. Des. 298,198.

The space between the first and second panels 132 and 134 in the area between the exterior depressions 122 and 123 may be filled with pillow fill or remain empty. If this space remains empty, the first and second panels 132 and 134 may rest against each other, as shown in FIG. 15.

As discussed above with respect to a Health Pillow, an additional panel 128 (or a third panel 128) is preferably attached by means of sewing, or the like, to the second panel 134 for covering the exterior depression 123 formed in the second panel 134. The additional panel 128 and the pillow fill 130 may substantially or completely cover the second panel 134, or just the exterior depression 123. The pillow fill 130 is enclosed between the additional panel 128 and the second panel 134 as the means used to support the central region of the additional panel 128 in a substantially flat position. If the pillow fill 130 covers or nearly covers the entire second panel 134 (as shown in FIG. 15), then the pillow fill 130 supports the outer regions of the additional panel 128, as well as the central region.

Figure 16:
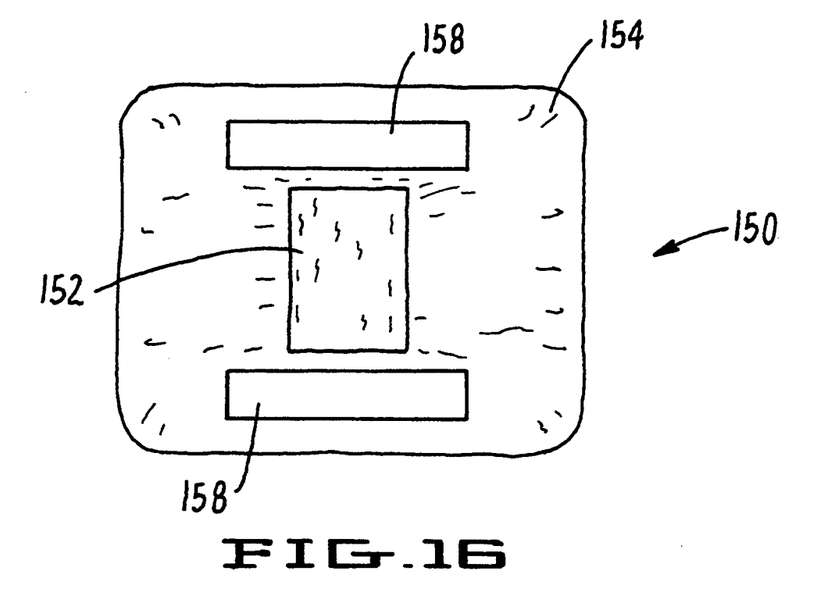
FIGS. 16 and 17 are top and bottom views of another embodiment of a two-sided pillow in accordance with the present invention.
Figure 17:
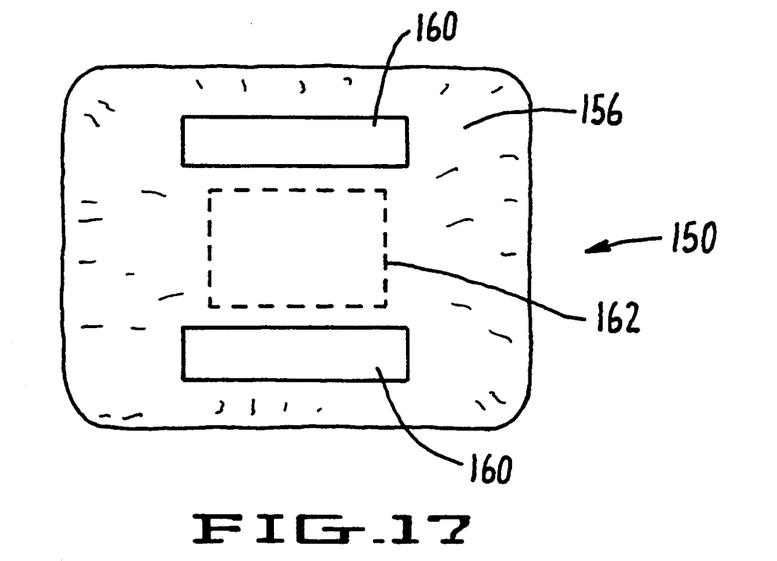

Referring to FIGS. 16 and 17, there is illustrated an alternative embodiment of a two-sided pillow 150 in accordance with the present invention. The two-sided pillow 150 is substantially identical to the two-sided pillow 120 in that it includes a central depression 152 on its first side 154, as shown in FIG. 16, and is relatively flat on the second side 156, as shown in FIG. 17. Unlike the two-sided pillow 120, however, the two-sided pillow 150 includes one or more pockets 158 on the first side 154. Alternatively or additionally, one or more pockets 160 may be included on the second side 156. The pockets 158 and 160 are for receiving pocket inserts, such as hot/cold packs, extra pillow fill or other stuffing to provide further support or comfort to the user's neck.

The pockets 158 and 160 may be constructed in the same manner as the pockets 12, 14, and 16 shown in FIGS. 1 through 8. In other words, the pockets 158 and 160 are preferably constructed from substantially rectangular panels having two long sides and two short sides. The lengths of the long sides of the rectangular panels are preferably about equal to one-third to one-half the length of the long sides of the pillow 150.

The pockets 158 and 160 are preferably positioned such that the long sides of the rectangular panels are parallel to and along the long sides of the pillow 150, as shown in FIGS. 16 and 17. In this position, the hot/cold packs which may be placed in the pockets 158 and 160 will provide a therapeutic effect to a user's neck when the user's head is rested on the pillow 150 in the manner discussed above.

The pockets 158 and 160 may be permanently attached to the pillow 150 by means of sewing or the like. Alternatively, the pockets 158 and 160 may be removably attached to the pillow 150 by means of VELCRO, snaps, or the like, such as is illustrated in FIG. 8.

As discussed above, a two-sided pillow, such as the two-sided pillow 150 of FIGS. 16 and 17, may be constructed by covering one of the central depressions of a Health Pillow with an additional panel (or "third panel"). The additional panel may cover the entire side of the Health Pillow or only the central depression. If the additional panel covers the entire side of the Health Pillow, then the pockets 160 are preferably attached to the additional panel. However, if the additional panel covers only the central depression, such as indicated by dotted line 162, then the pockets 160 are preferably attached to the second panel of the Health Pillow or partially attached to both the second panel and the additional panel. Either way, it may be said that the pockets 160 and 158 are attached near a side of one of the panels of the two-sided pillow 150, i.e., either the first, second, or additional (third) panels, such that the central regions of the panel are not covered.

Having thus described the invention, it is recognized that those skilled in the art may make various modifications or additions to the preferred embodiment chosen to illustrate the invention without departing from the spirit and scope of the present contribution to the art. Accordingly, it is to be understood that the protection sought and to be afforded hereby should be deemed to extend to the subject matter claimed and all equivalents thereof within the scope of the invention.

What is claimed is:

1. A two-sided pillow, comprising:
   a pillow having first and second opposed rectangular panels that are substantially identical and that each have two long sides and two short sides, each of the first and second panels having a central region, two side regions, and two neck support regions, the two side regions each having a greater area than each of the two neck support regions, the first and second panels being joined together along the two long sides and the two short sides and enclosing pillow fill therebetween, the first and second panels being further Joined together at the central region of each panel to form an exterior depression substantially at the center of each panel;
   a third panel attached to the second panel for covering the exterior depression formed in the second panel; and
   pillow fill enclosed between the third panel and the second panel;
   wherein, each of the side regions of the first panel are separated from a corresponding and opposed one of the side regions of the second panel by a first thickness and each of the side regions of the second panel are separated from the third panel by a second thickness, the first thickness being greater than the second thickness.

2. A two-sided pillow according to claim 1, wherein the exterior depressions are rectangular in shape.

3. A two-sided pillow according to claim 1, further comprising:
   a pocket for substantially enclosing a pocket insert, the pocket being attached near a side of one of the panels such that the central region of the one of the panels is exposed.

4. A two-sided pillow according to claim 3, wherein:
   the pocket comprises a substantially rectangular pocket panel having two long sides and two short sides.

5. A two-sided pillow according to claim 4, wherein:
   the length of the long sides of the rectangular pocket panel is at least about equal to one-third the length of the long sides of the first and second panels.

6. A two-sided pillow according to claim 4, wherein:
   the length of the long sides of the rectangular pocket panel is about equal to one-half the length of the long sides of the first and second panels.

* * * * *